US00PP14300P29

(12) United States Plant Patent
Sorensen

(10) Patent No.: US PP14,300 P2
(45) Date of Patent: Nov. 18, 2003

(54) OSTEOSPERMUM PLANT NAMED 'AKTERRA'

(50) Latin Name: *Osteospermum ecklonis*
Varietal Denomination: Akterra

(75) Inventor: Carl Aksel Kragh Sorensen, Aabyhøj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/232,900

(22) Filed: Aug. 31, 2002

(51) Int. Cl.[7] ..... A01H 5/00
(52) U.S. Cl. ..... Plt./360
(58) Field of Search ..... Plt./360

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Osteospermum plant named 'Akterra', characterized by its uniformly mounded plant habit; freely branching growth habit; freely flowering habit; dark green-colored foliage; and large inflorescences with orange-colored ray florets.

1 Drawing Sheet

Botanical classification/cultivar designation: *Osteospermum ecklonis* cultivar Akterra.

BACKGROUND OF THE INVENTION

The present Invention relates to a new and distinct cultivar of Osteospermum plant, botanically known as *Osteospermum ecklonis,* and hereinafter referred to by the name 'Akterra'.

The new Osteospermum is a product of a planned breeding program conducted by the Inventor in Aabyhøj, Denmark. The objective of the breeding program is to create new Osteospermum cultivars with uniform plant habit and interesting floret colors.

The new Osteospermum originated from a cross-pollination made by the Inventor during the spring of 1999 of the *Osteospermum ecklonis* cultivar Akope, disclosed in U.S. Plant Pat. No. 12,684, as the female, or seed, parent with a proprietary selection of *Osteospermum ecklonis* identified as code number 9619, not patented, as the male, or pollen, parent. The new Osteospermum was discovered and selected by the Inventor as a single flowering plant within the progeny of the stated cross-pollination grown in a controlled environment in Aabyhøj, Denmark in 2000.

Asexual reproduction of the new Osteospermum by vegetative tip cuttings was first conducted in Aabyhøj, Denmark in February, 2000. Asexual reproduction by cuttings has shown that the unique features of this new Osteospermum are stable and reproduced true to type in successive generations.

SUMMARY OF THE INVENTION

The cultivar Akterra has not been observed under all possible environmental conditions. The phenotype may vary somewhat with variations in environment such as temperature and light intensity without, however, any variance in genotype.

The following traits have been repeatedly observed and are determined to be the unique characteristics of 'Akterra'. These characteristics in combination distinguish 'Akterra' as a new and distinct Osteospermum:

1. Uniformly mounded plant habit.
2. Freely branching growth habit; full and dense plants.
3. Freely flowering habit.
4. Dark green-colored foliage.
5. Large inflorescences with orange-colored ray florets.

The new Osteospermum can be compared to plants of the female parent, the cultivar Akope. In side-by-side comparisons conducted in Aabyhøj, Denmark, plants of the new Osteospermum differed primarily from plants of the cultivar Akope in the following characteristics:

1 . Plants of the new Osteospermum had darker green-colored leaves than plants of the cultivar Akope.
2. Inflorescences of plants of the new Osteospermum were larger than inflorescences of plants of the cultivar Akope.
3. Ray florets of plants of the new Osteospermum were orange in color whereas ray florets of plants of the cultivar Akope were salmon pink in color.

The new Osteospermum can be compared to plants of the male parent, the selection 9619. In side-by-side comparisons conducted in Aabyhøj, Denmark, plants of the new Osteospermum differed primarily from plants of the selection 9619 in the following characteristics:

1. Plants of the new Osteospermum had darker green-colored leaves than plants of the selection 9619.
2. Plants of the new Osteospermum were more freely branching than plants of the selection 9619.
3. Ray florets of plants of the new Osteospermum were orange in color whereas ray florets of the selection 9619 were light pink in color.

The new Osteospermum can also be compared to plants of the cultivar Maputo, not patented. In side-by-side comparisons conducted in Encinitas, Calif., plants of the new Osteospermum differed from plants of the cultivar Maputo in the following characteristics:

1. Plants of the new Osteospermum were more compact than plants of the cultivar Maputo.
2. Plants of the new Osteospermum had darker green-colored leaves than plants of the cultivar Maputo.
3. Ray florets of plants of the new Osteospermum were orange in color whereas ray florets of plants of the cultivar Maputo were yellow in color.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photograph at the top of the sheet comprises a side perspective view of a typical flowering plant of 'Akterra' grown in container.

The photograph at the bottom of the sheet is a close-up view of typical leaves, inflorescences and inflorescence buds of 'Akterra'.

DETAILED BOTANICAL DESCRIPTION

In the following description, color references are made to The Royal Horticultural Society Colour Chart, 1995 Edition, except where general terms of ordinary dictionary significance are used.

The aforementioned photographs, following observations and measurements describe plants grown during the winter and spring in Encinitas, Calif., in an outdoor nursery and under conditions which approximate those generally used in commercial Osteospermum production. Plants were grown in 15-cm containers and pinched once. During the production of the plants, day temperatures were about 24° C., night temperatures were about 19° C., and light levels were about 4,000 foot-candles. Measurements and numerical values represent averages of typical flowering plants about 21 weeks after planting.

Botanical classification: *Osteospermum ecklonis* cultivar Akterra.

Parentage:

*Female, or seed, parent.*—*Osteospermum ecklonis* cultivar Akope, disclosed in U.S. Plant Pat. No. 12,684.

*Male, or pollen, parent.*—Proprietary selection of *Osteospermum ecklonis* identified as code number 9619, not patented.

Propagation:

*Type.*—Terminal cuttings.

*Time to initiate rooting.*—Summer: About 12 days at 18° C. Winter: About 14 days at 18° C.

*Time to develop roots.*—About 26 days at 18° C.

*Root description.*—Fibrous, fine; white in color.

*Rooting habit.*—Freely branching.

Plant description:

*Appearance.*—Perennial herbaceous container and garden plant. Uniformly mounded plant habit; upright and somewhat outwardly spreading; inverted triangle. Freely branching, about twelve lateral branches develop after pinching; dense and full plants. Vigorous growth habit.

*Plant height.*—About 46 cm.

*Plant width or area of spread.*—About 50 cm.

*Lateral branches.*—Length: About 41.5 cm. Diameter: About 6.5 mm. Internode length: About 1.5 cm. Aspect: Erect. Strength: Strong. Texture: Glabrous, smooth. Color: 144A.

*Foliage description.*—Arrangement: Alternate; simple. Number of leaves per lateral branch: About 20. Length: About 4.2 cm. Width: About 2 cm. Shape: Elliptic. Apex: Acute. Base: Attenuate. Margin: Irregularly lobed. Venation pattern: Pinnate. Texture: Somewhat coarse, leathery, glandular and glabrous. Color: Young foliage, upper surface: 147A. Young foliage, lower surface: 146A. Fully expanded foliage, upper and lower surfaces: 147A. Venation, upper and lower surfaces: 146A. Petiole: Length: About 1.3 cm. Diameter: About 3 mm. Texture, upper and lower surfaces: Glabrous. Color: Upper surface: 144A. Lower surface: 146B.

Inflorescence description:

*Appearance.*—Terminal and axillary inflorescences held above and beyond the foliage on moderately strong peduncles. Composite inflorescence form, radially symmetrical, with ligulate-shaped ray florets and disc florets massed at the center; ray and disc florets develop acropetally on a capitulum. Inflorescences persistent. Inflorescences face mostly upright.

*Flowering response.*—Plants flower continuous and freely from the spring through the fall.

*Postproduction longevity.*—Inflorescences maintain good color and substance for about seven to ten days on the plant when grown in an outdoor environment.

*Quantity of Inflorescences.*—Freely flowering; at one time, about 80 open inflorescences and buds per plant.

*Fragrance.*—Slightly fragrant; sour.

*Inflorescence bud (at stage of showing color).*—Length: About 2.2 cm. Diameter: About 1.2 cm. Shape: Ovoid. Color, ray florets, lower or outer surface: More gray than 165B.

*Inflorescence size.*—Diameter: About 8.5 cm. Depth (height): About 3 cm. Disc diameter: About 1.7 cm. Receptacle diameter: About 2 cm. Receptacle height: About 1.3 cm.

*Ray florets.*—Length: About 4.2 cm. Width: About 7 mm. Shape: Ligulate. Apex: Emarginate. Base: Attenuate. Margin: Entire. Texture: Velvety. Orientation: Initially upright then about 45° from vertical. Number of ray florets per inflorescence: About 28 in a single whorl. Color: When opening, upper surface: 31C. When opening, lower surface: Ground color, 23C, with longitudinal stripes, 165B to 177C. Fully opened, upper surface: Towards apex, 167A; mid-section, 167B; towards base, 167C; color becoming closer to 163B to 163C with subsequent development. Fully opened, lower surface: Ground color, 162A, with longitudinal stripes, 165A to 165B.

*Disc florets.*—Shape: Tubular, elongated. Apex: Five-pointed. Length: About 1.3 cm. Width: At apex: About 4 mm. At base: Less than 1 mm. Number of disc florets per inflorescence: About 120. Color: Immature: 200B. Mature: Apex: 165A. Mid-section: 173D. Base: 155A.

*Phyllaries.*—Length: About 1.1 cm. Diameter: About 1 mm. Shape: Linear. Apex: Acuminate. Base: Fused. Margin: Entire. Texture, upper and lower surfaces: Slightly coarse with tiny hairs. Number per inflorescence: About 26 in a single whorl. Color: Upper surface: 144A. Lower surface: 146B.

*Peduncles.*—Length, terminal peduncle: About 8.75 cm. Length, third peduncle: About 9.75 cm. Diameter: About 2.5 mm. Angle: Terminal peduncles, erect; secondary and tertiary peduncles, about 25° from vertical. Strength: Strong. Texture: Coarse with tiny scattered short hairs. Color: 146A.

*Reproductive organs.*—Androecium: Present on disc florets only. Stamen number: Five per floret; fused around style. Anther shape: Oblong. Anther size:

About 3 mm by 1 mm. Anther color: 200A. Pollen amount: Moderate. Pollen color: 23A. Gynoecium: Present on both ray and disc florets. Pistil number: One per floret. Pistil length: About 1.2 cm. Stigma shape: Two-parted. Stigma color: 200A. Style length: About 4 mm. Style color: 165C. Ovary color: 157A.

*Seed/fruit.*—Seed and fruit production has not been observed.

Disease/pest resistance: Resistance to pathogens and pests common to Osteospermums has not been observed on plants grown under commercial greenhouse or outdoor conditions.

Temperature tolerance: Plants of the new Osteospermum have been observed to tolerate temperatures from 0 to 40° C.

It is claimed:

1. A new and distinct cultivar of Osteospermum plant named 'Akterra', as illustrated and described.

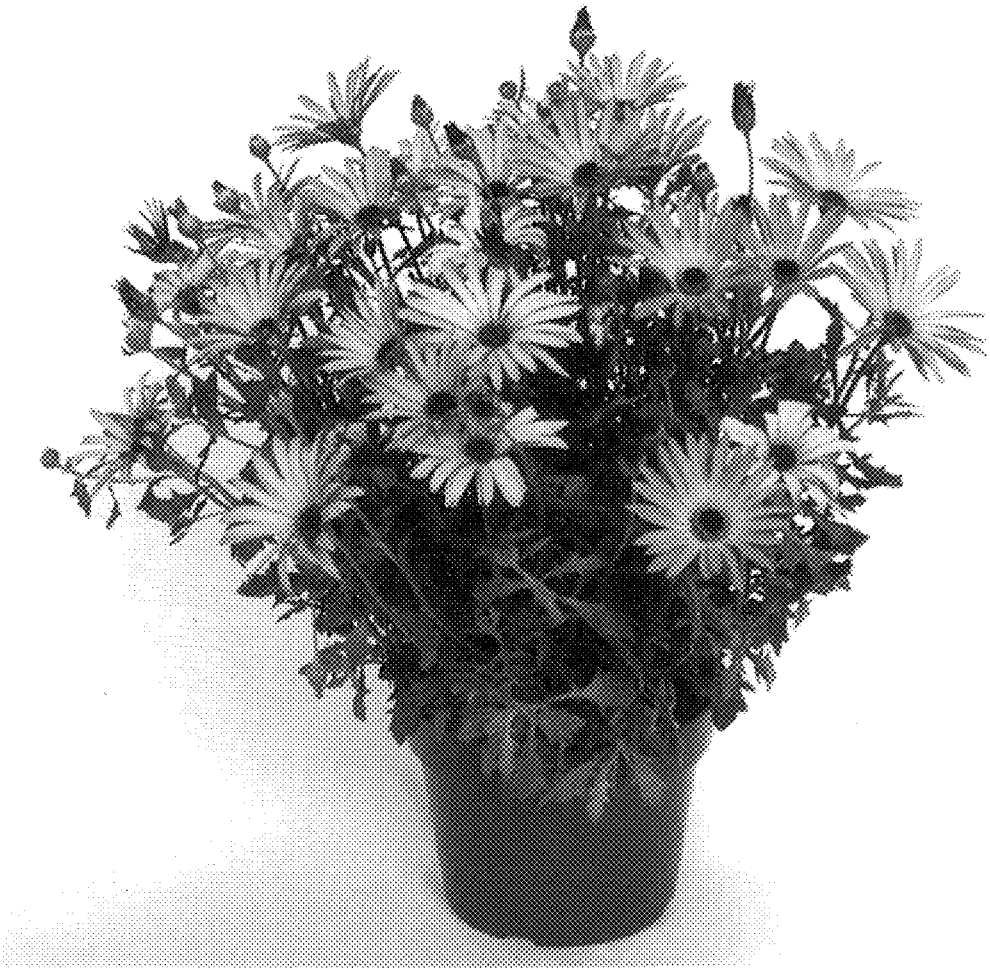
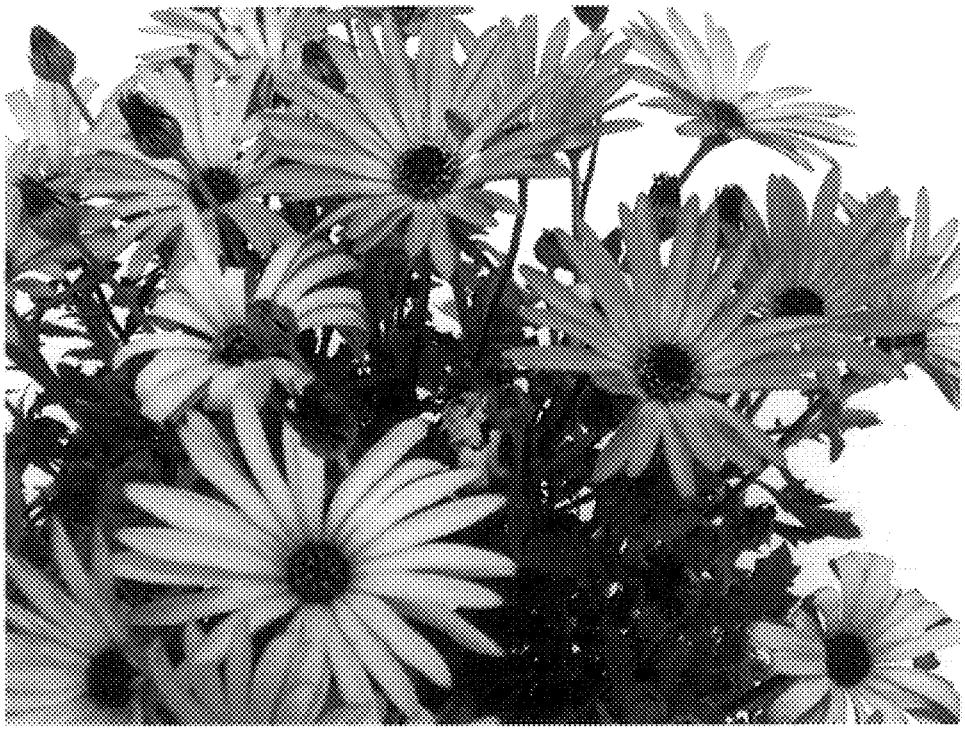

* * * * *